(12) United States Patent
Tanaka

(10) Patent No.: US 8,480,297 B2
(45) Date of Patent: Jul. 9, 2013

(54) EAR THERMOMETER

(75) Inventor: Hideki Tanaka, Sapporo (JP)

(73) Assignee: BIO ECHO NET inc, Sapporo-shi (JP)

( * ) Notice: Subject to any disclaimer, the term of this patent is extended or adjusted under 35 U.S.C. 154(b) by 234 days.

(21) Appl. No.: 12/995,897

(22) PCT Filed: May 20, 2009

(86) PCT No.: PCT/JP2009/059273
§ 371 (c)(1),
(2), (4) Date: Feb. 17, 2011

(87) PCT Pub. No.: WO2009/147947
PCT Pub. Date: Dec. 10, 2009

(65) Prior Publication Data
US 2011/0164654 A1   Jul. 7, 2011

(30) Foreign Application Priority Data
Jun. 3, 2008   (JP) .................... 2008-145522

(51) Int. Cl.
*G01K 7/00* (2006.01)
*G01K 1/00* (2006.01)

(52) U.S. Cl.
USPC ............ 374/141; 374/178; 374/170; 374/163

(58) Field of Classification Search
USPC .................. 374/141, 178, 170, 163
See application file for complete search history.

(56) References Cited

U.S. PATENT DOCUMENTS

| 5,829,878 | A | 11/1998 | Weiss et al. | |
| 6,357,909 | B1 | 3/2002 | Watanabe | |
| 7,301,522 | B2 * | 11/2007 | Ko | 345/102 |
| 2006/0197735 | A1 * | 9/2006 | Vuong et al. | 345/102 |
| 2006/0274026 | A1 * | 12/2006 | Kerofsky | 345/102 |
| 2006/0291535 | A1 * | 12/2006 | Craig et al. | 374/208 |
| 2007/0104246 | A1 * | 5/2007 | Tseng | 374/163 |
| 2008/0055230 | A1 * | 3/2008 | Jang et al. | 345/102 |
| 2008/0075144 | A1 * | 3/2008 | Tseng | 374/170 |
| 2009/0091265 | A1 * | 4/2009 | Song et al. | 315/185 R |
| 2009/0175317 | A1 * | 7/2009 | Chan et al. | 374/170 |
| 2009/0225230 | A1 * | 9/2009 | Arroyo et al. | 348/730 |
| 2011/0031903 | A1 * | 2/2011 | Nguyen Hoang et al. | 315/309 |

FOREIGN PATENT DOCUMENTS

| CN | 1239544 A | 12/1999 |
| EP | 0937972 A1 | 8/1999 |
| JP | 11-108770 | 4/1999 |

(Continued)

*Primary Examiner* — Mirellys Jagan
(74) *Attorney, Agent, or Firm* — Marvin A. Motsenbocker; Mots Law, PLLC

(57) ABSTRACT

The present invention provides an ear thermometer that irradiates liquid crystal with backlight without increasing a battery capacity, to make a body temperature displayed with the liquid crystal easily visible even in a dark place. An MCU 1 displays a body temperature measured by a body temperature measuring part (3) on a liquid crystal display part (5), controls, through input/output ports (P1, P2), a backlight emitting part (7) in such a way that the light quantity of the backlight irradiating the liquid crystal display part (5) from the backlight emitting part (7) is maximized for a first predetermined time, controls the backlight emitting part (7) in such a way that the quantity of the backlight keeps, for a second predetermined time that follows the first predetermined time, a predetermined level that is lower than the maximum, and controls the backlight emitting part (7) in such a way that the quantity of the backlight is zeroed after the second predetermined time elapses.

12 Claims, 12 Drawing Sheets

FOREIGN PATENT DOCUMENTS

| | | |
|---|---|---|
| JP | 2001-016793 | 1/2001 |
| JP | 2001-285471 | 10/2001 |
| JP | 2005-065866 | 3/2005 |
| JP | 2007-111363 | 5/2007 |
| TW | 424139 B | 3/2001 |
| TW | I255128 B | 5/2006 |
| WO | 99/13305 A1 | 3/1999 |

* cited by examiner

EAR THERMOMETER

TECHNICAL FIELD

The present invention relates to an ear thermometer for sensing infrared rays radiated from an ear hole depth and thereby measuring a body temperature, and particularly, to an ear thermometer capable of emitting backlight in a power saving manner so that the body temperature displayed with liquid crystal is easily visible even in a dark place.

BACKGROUND TECHNOLOGY

An ear thermometer has a probe provided with an infrared sensor. The probe is inserted into an ear and the ear thermometer can measure a body temperature within a short time such as one second. Accordingly, the ear thermometer is very useful to measure the body temperature of an infant or a child who easily cries, or is asleep, or keeps moving.

The body temperature measured by the ear thermometer is generally displayed with liquid crystal from viewpoints of small size, low power consumption, light weight, and the like. The liquid crystal displaying is acceptable in a bright place but it is hardly visible in a dark place. In particular, measuring the body temperature of an infant or a child is frequently carried out in a relatively dark place when the infant or child is sleeping. It is important, therefore, to make the displayed temperature visible even in a dark place.

To make the body temperature displayed with liquid crystal visible even in a dark place, irradiating the liquid crystal with backlight is effective. Irradiating liquid crystal with backlight, however, consumes large power. For example, the backlight for liquid crystal of the ear thermometer consumes 75% or more of total power consumption. This raises a necessity of increasing the capacity of a battery of the ear thermometer. For this, a conventional ear thermometer must increase a normally used button-type or AAA-size battery to two pieces.

As mentioned above, the conventional ear thermometer makes a body temperature displayed with liquid crystal visible even in a dark place by irradiating the liquid crystal with backlight. The backlight consumes large power, and therefore, needs to increase the number of batteries to use. This results in increasing the price, size, and weight of the ear thermometer, thereby deteriorating the usability of the ear thermometer. If the number of batteries is not increased, the large power consumption by backlight forces the battery to be frequently replaced with a new one, thereby deteriorating the usability and practicality of the ear thermometer.

RELATED ART DOCUMENTS

Patent Documents

[Patent Document 1] Japanese Unexamined Patent Application Publication No. 2007-111363
[Patent Document 2] Japanese Unexamined Patent Application Publication No. 2005-65866

OUTLINE OF INVENTION

Problems to be Solved by Invention

In consideration of the above-mentioned technical problems, an object of the present invention is to provide an ear thermometer that irradiates liquid crystal with backlight without increasing a battery capacity, to make a body temperature displayed with the liquid crystal easily visible even in a dark place.

Means to Solve the Problems

The present invention provides an ear thermometer including a body temperature measuring part to sense infrared rays radiated from an ear hole depth and thereby measure a body temperature, a liquid crystal display part to display the body temperature measured by the body temperature measuring part, a backlight emitting part to irradiate the liquid crystal display part with backlight, and a driving-controlling part to display the body temperature measured by the body temperature measuring part on the liquid crystal display part and drive the backlight emitting part so that the quantity of the backlight that irradiates the liquid crystal display part from the backlight emitting part may gradually change from a maximum level to an off level.

The above-mentioned ear thermometer irradiates a body temperature displayed on the liquid crystal display part with backlight by controlling the backlight emitting part in such a way that the quantity of the backlight gradually changes from a maximum level to an off level, thereby greatly reducing power consumed by the backlight. The measured body temperature displayed on the liquid crystal display part is irradiated with the backlight of the maximum level at first, so that the user can clearly see the body temperature displayed on the liquid crystal display part even in the dark.

The present invention also provides an ear thermometer including a body temperature measuring part to sense infrared rays radiated from an ear hole depth and thereby measure a body temperature, a liquid crystal display part to display the body temperature measured by the body temperature measuring part, a backlight emitting part to irradiate the liquid crystal display part with backlight, and a driving-controlling part to display the body temperature measured by the body temperature measuring part on the liquid crystal display part, drive and control the backlight emitting part so that, for a first predetermined time from the start of the display, the light quantity of the backlight irradiating the liquid crystal display part from the backlight emitting part is at a maximum level, drive and control the backlight emitting part so that, for a second predetermined time following the first predetermined time, the light quantity of the backlight irradiating the liquid crystal display part from the backlight emitting part is at a predetermined level lower than the maximum level, and drive and control the backlight emitting part so that, once the second predetermined time elapses, the light quantity of the backlight irradiating the liquid crystal display part from the backlight emitting part is zeroed.

The above-mentioned ear thermometer maximizes the quantity of the backlight for the first predetermined time after displaying a measured body temperature on the liquid crystal display part, keeps for the second predetermined time following the first predetermined time the quantity of the backlight at the predetermined level lower than the maximum level, and zeroes the quantity of the backlight once the second predetermined time elapses. This results in greatly reducing power consumption by the backlight. The measured body temperature displayed on the liquid crystal display part is irradiated with the backlight of the maximum quantity for the first predetermined time, and therefore, the user can clearly view the body temperature displayed on the liquid crystal display part even in a dark place.

In the above-mentioned ear thermometer, the driving-controlling part controls the backlight emitting part so that, for the first predetermined time, the liquid crystal display part is continuously irradiated with the backlight, intermittently controls the backlight emitting part at a predetermined ON/OFF ratio so that, for the second predetermined time, the liquid crystal display part is intermittently irradiated with the backlight at the predetermined ON/OFF ratio, and controls the backlight emitting part so that, once the second predetermined time elapses, the backlight irradiating the liquid crystal display part is turned off.

In this way, the above-mentioned ear thermometer continuously emits the backlight for the first predetermined time, intermittently emits the backlight at the predetermined ON/OFF ratio for the second predetermined time, and once the second predetermined time elapses, turns off the backlight. This greatly reduces power consumption by the backlight. The measured body temperature displayed on the liquid crystal display part is continuously irradiated with the backlight for the first predetermined time, and therefore, the user can clearly view the displayed body temperature even in the dark.

According to the above-mentioned ear thermometer, the backlight emitting part has a light emitting diode.

The ear thermometer can be miniaturized because the backlight emitting part uses the light emitting diode.

In the above-mentioned ear thermometer, the intermittent drive control on the backlight emitting part by the driving-controlling part at the predetermined ON/OFF ratio may be carry out at a repetition frequency of 30 Hz or over.

When the ear thermometer employs the repetition frequency of 30 Hz or over to carry out the intermittent drive control of the predetermined ON/OFF ratio on the backlight emitting part, human eyes continuously view the backlight from the LED that is intermittently turned on and off and sense no discontinuation of the LED light, i.e., the blinking of the LED light.

The above-mentioned ear thermometer also includes a power supply control part that intermittently carries out power supply to the body temperature measuring part for a predetermined time from the start of power supply to the body temperature measuring part by gradually increasing a predetermined small ON/OFF ratio to a predetermined large ON/OFF ratio, and after the predetermined time elapses, continuously carries out power supply to the body temperature measuring part.

In this case, the ear thermometer intermittently carries out power supply to the body temperature measuring part for the predetermined time from the start of power supply to the body temperature measuring part by gradually increasing the predetermined small ON/OFF ratio to the predetermined large ON/OFF ratio, and after the predetermined time elapses, continuously carries out power supply to the body temperature measuring part. The ear thermometer, therefore, can smoothly conduct a power ON soft start operation of power supply to the body temperature measuring part and prevent operation of the control system from being destabilized.

The above-mentioned ear thermometer includes a power supply control part that supplies power to the body temperature measuring part intermittently at a first predetermined ON/OFF ratio for a first predetermined time from the start of power supply, intermittently at a second predetermined ON/OFF ratio that is larger than the first predetermined ON/OFF ratio for a second predetermined time that follows the first predetermined time, intermittently at a third predetermined ON/OFF ratio that is larger than the second predetermined ON/OFF ratio for a third predetermined time that follows the second predetermined time, and continuously after the third predetermined time elapses.

In this case, the ear thermometer supplies power to the body temperature measuring part intermittently at the first predetermined ON/OFF ratio for the first predetermined time after the start of power supply, intermittently at the larger second predetermined ON/OFF ratio for the second predetermined time, intermittently at the further larger third predetermined ON/OFF ratio for the third predetermined time, and continuously after the third predetermined time elapses. The ear thermometer, therefore, can smoothly conduct a power ON soft start operation of power supply to the body temperature measuring part, correctly measure a body temperature, and prevent operation of the control system from being destabilized.

Effect of Invention

The present invention irradiates a body temperature displayed with liquid crystal with backlight by controlling the backlight emitting part in such a way that the quantity of the backlight gradually changes from a maximum level to an off level, thereby greatly reducing power consumption by the backlight. The body temperature displayed with liquid crystal is irradiated with the backlight of maximum quantity at least at first, so that the user can clearly view the displayed body temperature even in a dark place.

According to the present invention, power supply to the body temperature measuring part for a predetermined time from the start of power supply to the body temperature measuring part is intermittently carried out by gradually increasing a predetermined small ON/OFF ratio to a predetermined large ON/OFF ratio. After the predetermined time elapses, power supply to the body temperature measuring part is continuously carried out. This results in correctly measuring a body temperature and preventing operation of the control system from being destabilized.

EMBODIMENTS

Embodiments of the present invention will be explained in detail with reference to the drawings.

Figure 1:
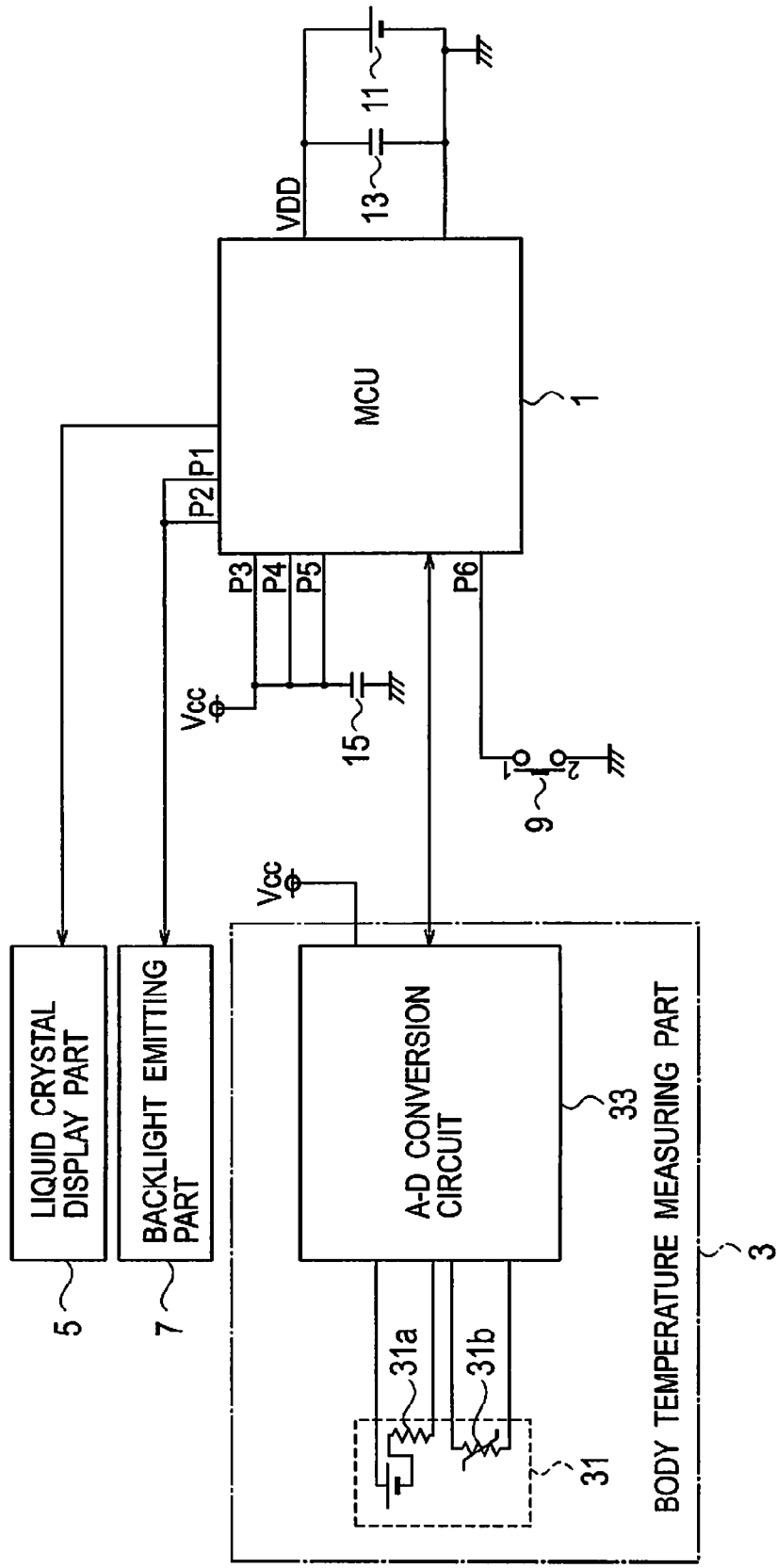
FIG. 1 is a block diagram illustrating a general configuration of a control system of an ear thermometer according to an embodiment of the present invention.

FIG. 1 illustrates an ear thermometer according to an embodiment of the present invention. This ear thermometer has a microcontroller (hereinafter referred to as MCU) 1 using a microprocessor to control overall operation. The MCU 1 is connected to a body temperature measuring part 3 to measure the body temperature of an object, a liquid crystal display part 5 to display the body temperature measured by the body temperature measuring part 3 with liquid crystal, and a backlight emitting part 7 to emit backlight to the liquid crystal display part 5 to make the liquid crystal display part 5 brighter.

The MCU 1 receives a voltage VDD from a power source battery 11 such as a button-type lithium battery and operates with the voltage. Connected in parallel with the battery 11 is a capacitor 13 to reduce a power source impedance of the battery 11.

The body temperature measuring part 3 has a thermopile-type infrared sensor 31 and an analog-digital conversion circuit (A-D conversion circuit) 33 to convert an analog signal corresponding to a body temperature of an object detected by the infrared sensor 31 into a digital signal and supply the digital signal as a digital body temperature signal to the MCU 1. The infrared sensor 31 consists of a thermopile 31A that is indicated with an equivalent circuit having a battery and a resistor that are connected in series, and a thermistor 31B for temperature compensation.

The body temperature measuring part 3 receives a voltage VCC as a power source voltage under the control of the MCU 1 and operates with the voltage. The voltage VCC is generated under the control of the MCU 1 at parallel-connected input/output ports P3, P4, and P5 of the MCU 1 and is supplied to the body temperature measuring part 3. The parallel-connected input/output ports P3, P4, and P5 of the MCU 1 are connected to a capacitor 15. The capacitor 15 is to decouple the A-D conversion circuit 33 and reduce an impedance of the power source to supply the operation voltage VCC to the A-D conversion circuit 33.

The MCU 1 is connected through an input/output port P6 to a start switch 9. When the start switch 9 is operated, an interrupt is issued to the MCU 1, so that the MCU 1 conducts a power supply operation, i.e., a power ON operation with respect to the body temperature measuring part 3 to start a body temperature measuring operation.

The MCU 1 is put in a standby state a predetermined time after the battery 11 is installed. In the standby state, the MCU 1 stops an internal oscillator to minimize current consumption by the MCU 1. The minimum power consumption in the standby state is the sum of an operation current of an internal voltage detection circuit of the MCU 1 and a leakage current of internal circuits of the MCU 1. In the standby state, the MCU 1 accepts only an interrupt from the start switch 9 so that, as mentioned above, the MCU 1 carries out the power ON start operation with respect to the body temperature measuring part 3 to start a body temperature measuring operation.

The backlight emitting part 7 has a light emitting diode (hereinafter referred to as LED). To reduce power consumption of backlight from the LED, the MCU 1 generates LED irradiation timing. For this, the backlight emitting part 7 is connected to open-drain input/output ports P1 and P2. To reduce the power consumption of the LED, the LED irradiation timing is generated in such a way that the LED irradiates a measured body temperature with a maximum light quantity only for a predetermined time, for example, 10 seconds just after the completion of a body temperature measurement of an object, so that the body temperature is brightly displayed and easily visible. At a moment when the object should have read the brightly displayed body temperature, the light quantity of the LED is reduced to an extent that the displayed body temperature is visible, and after a predetermined time, for example, 30 seconds, the LED is turned off to stop the backlight irradiation.

Figure 2:
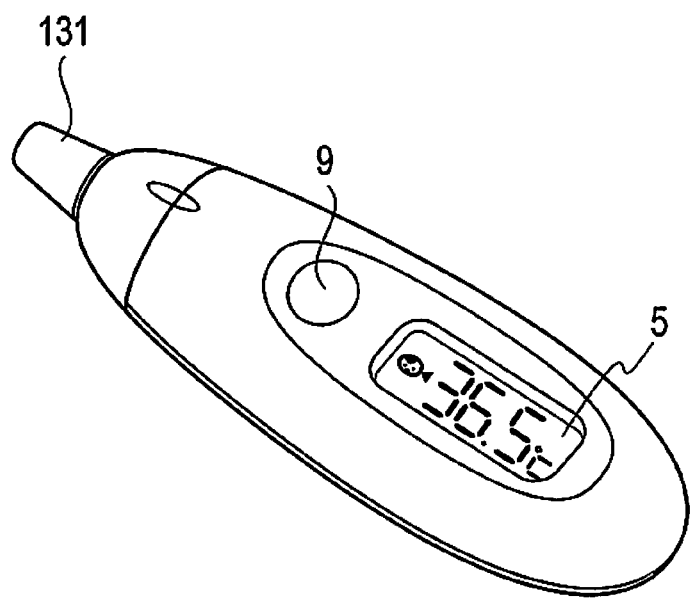
FIG. 2 is a perspective view illustrating an external appearance of the ear thermometer of the embodiment illustrated in FIG. 1.

As illustrated in FIG. 2, the ear thermometer has a long and narrow shape so that it is easy to grasp and measure the body temperature of an object. It has a probe 131 at an end thereof and the liquid crystal display part 5 and start switch 9 at the middle thereof.

The probe 131 is to measure the body temperature of an object and is inserted into an ear hole of the object. The probe 131 incorporates the infrared sensor 31. When the probe 131 is inserted into an ear hole of an object, the infrared sensor 31 in the probe 131 senses infrared rays radiated from an ear hole depth of the object and supplies a detection signal to the A-D conversion circuit 33. The A-D conversion circuit 33 converts the detection signal from the infrared sensor 31, i.e., an analog signal corresponding to the body temperature of the object into a digital signal and supplies the digital signal to the MCU 1.

Figure 3:
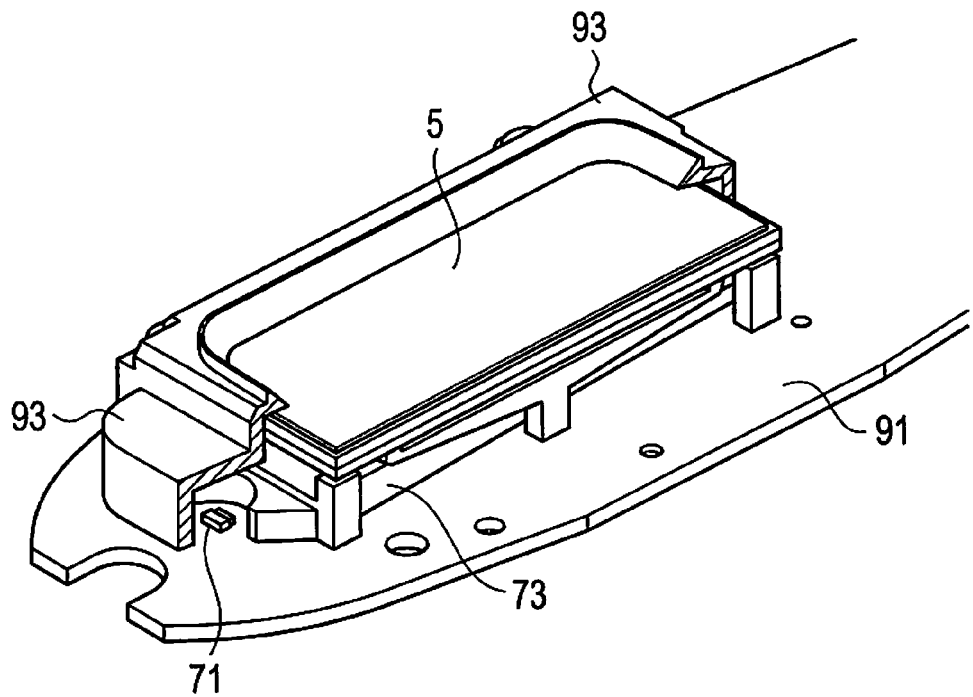
FIG. 3 is a perspective view illustrating part of an internal structure of the ear thermometer of the embodiment illustrated in FIGS. 1 and 2.
Figure 4:
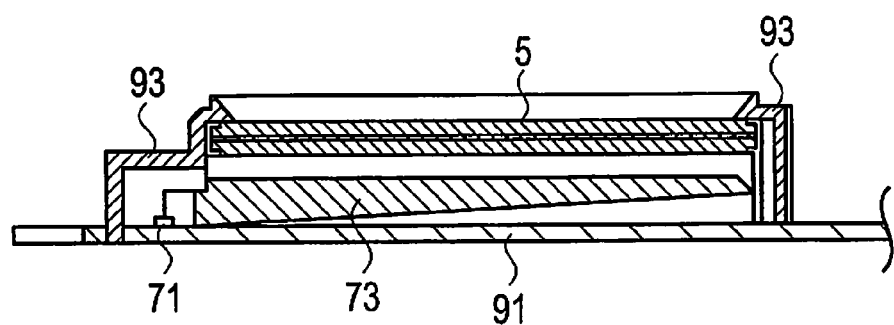
FIG. 4 is a sectional side view illustrating part of the internal structure of the ear thermometer of the embodiment illustrated in FIGS. 1 and 2.

As illustrated in FIGS. 3 and 4, among essential parts of the ear thermometer according to the embodiment, the liquid crystal display part 5 and the light emitting diode (LED) 71 of the backlight emitting part 7 are arranged on a board 91. More precisely, the board 91 has a frame 93 having a window to which the liquid crystal display part 5 is attached.

As is apparent in FIG. 4, under the liquid crystal display part 5, i.e., between the liquid crystal display part 5 and the board 91, a light guide 73 is arranged. On the left side of the light guide 73 in FIGS. 3 and 4, the LED 71 is arranged on the board 91. Light from the LED 71 enters a left side face (FIG. 4) of the light guide 73, is equally dispersed along an inclined bottom face of the light guide 73, and is reflected upwardly so that the reflected light serves as backlight for the liquid crystal display part 5, to evenly entirely irradiate the liquid crystal display part 5 from below and make the liquid crystal display part 5 bright and easily visible.

Figure 5:
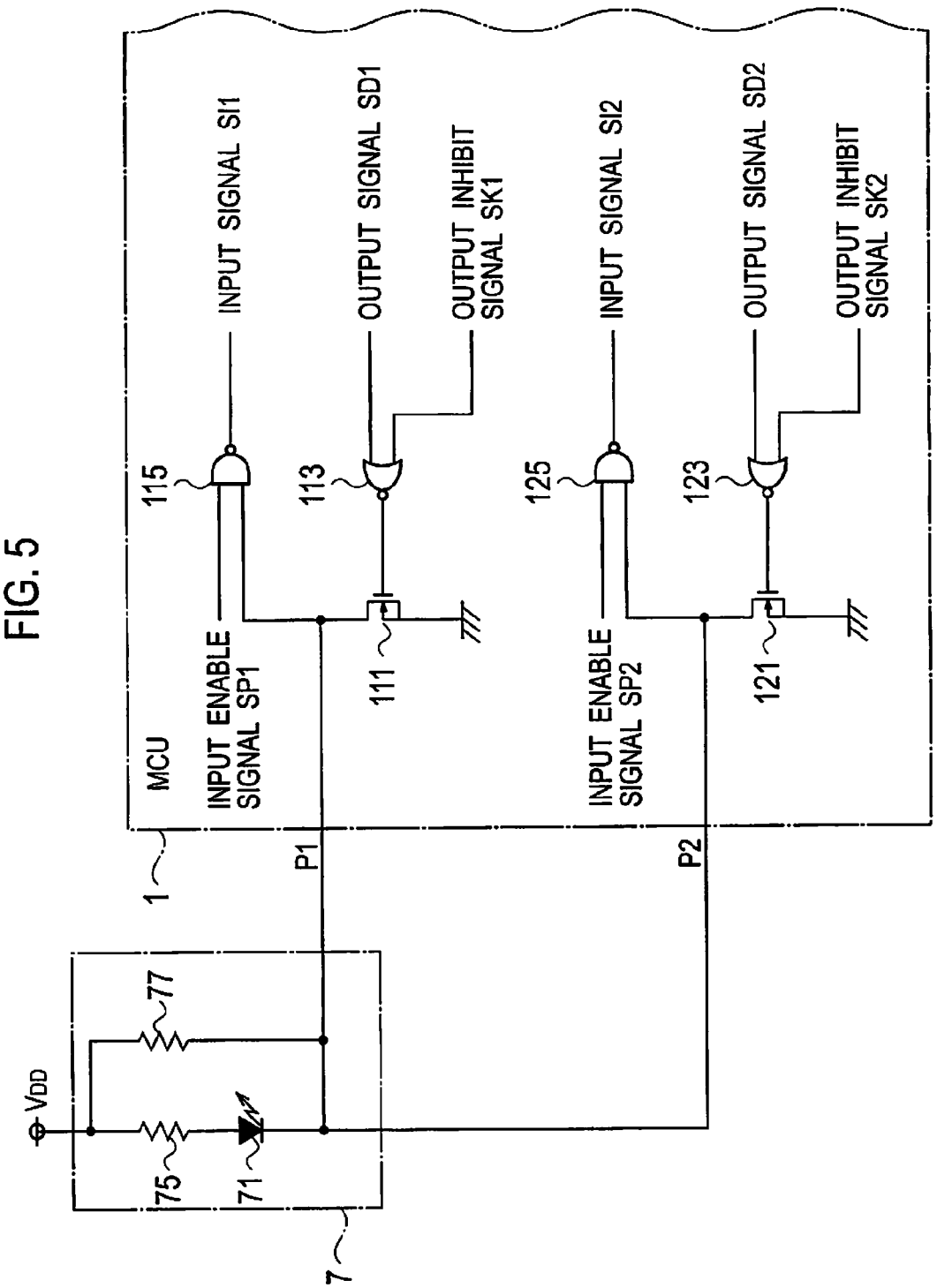
FIG. 5 is a circuit diagram illustrating a concrete example of a backlight emitting part and the details of the inside of an input/output port of an MCU connected to the backlight emitting part arranged in the ear thermometer of the embodiment illustrated in FIG. 1.

As illustrated in FIG. 5, in the backlight emitting part 7, an anode of the LED 71 is connected through a resistor 75 to the operation voltage VDD of the MCU 1 and a cathode of the LED 71 is connected to the input/output ports P1 and P2 of the MCU 1. Ends of the series-connected LED 71 and resistor 75 are connected in parallel with a resistor 77. The resistor 75 regulates a current passed to the LED 71. The resistor 77 is a pull-up resistor to prevent the input/output ports P1 and P2 of the MCU 1 from being destabilized.

The input/output ports P1 and P2 of the MCU 1 connected to the cathode of the LED 71 are connected to drains of re-channel MOSFETs 111 and 121, respectively, in the MCU 1. Sources of the MOSFETs 111 and 121 are grounded and gates thereof are connected to outputs of NOR circuits 113 and 123, respectively. First inputs of the NOR circuits 113 and 123 receive output signals SD1 and SD2, respectively, and second inputs thereof receive output inhibit signals SK1 and SK2, respectively.

The drains of the MOSFETs 111 and 121 are connected to first inputs of NAND circuits 115 and 125, respectively. Second inputs of the NAND circuits 115 and 125 receive input enable signals SP1 and SP2, respectively. Outputs of the NAND circuits 115 and 125 provide the inside of the MCU 1 with input signals SI1 and SI2, respectively. These input signals are external input signals from the input/output ports P1 and P2.

With the above-mentioned circuit configuration, power consumption reducing operation for the backlight irradiation of the LED 71 will be explained with reference to the LED irradiation timing of FIG. 6.

The body temperature of an object measured by the body temperature measuring part 3 is supplied through the MCU 1 to the liquid crystal display part 5 and is displayed on the liquid crystal display part 5. The body temperature simply displayed with liquid crystal is hardly visible in the dark. Accordingly, light from the LED 71 of the backlight emitting part 7 is used as backlight to irradiate the liquid crystal display part 5 so that the displayed temperature becomes bright and easily visible in the dark. Irradiating the liquid crystal display part 5 with the backlight from the LED 71 greatly increases power consumption and shortens the service life of the battery 11 that supplies the voltage VDD. In some cases, the number of batteries must be increased.

Figure 6:
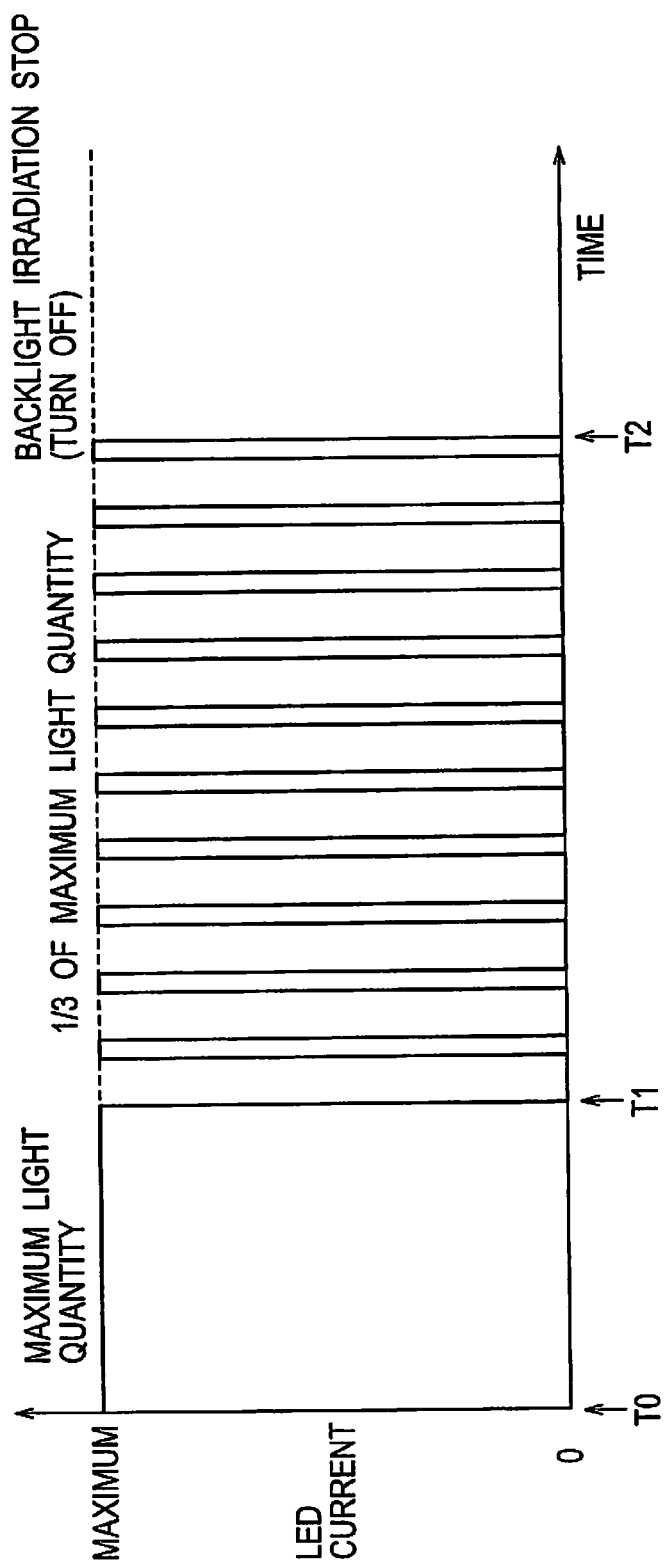
FIG. 6 is a view illustrating LED irradiation timing to conduct a power consumption reduction operation on backlight irradiation.

To avoid the shortening of the service life of the battery or an increase in the number of batteries, and at the same time, to make the liquid crystal display part 5 easily visible with backlight, the embodiment controls the LED 71 according to the LED irradiation timing illustrated in FIG. 6 when irradiating the liquid crystal display part 5 with the backlight from the LED 71.

More precisely, the LED irradiation timing makes the body temperature displayed on the liquid crystal display part 5 bright and easily visible even in the dark with the use of the backlight. Once the object reads the brightly displayed body temperature, it is not necessary to brightly irradiate the same with the backlight, and therefore, the LED irradiation timing dims the backlight after a time in which the object should have read the body temperature, thereby avoiding the shortening of the service life of the battery or an increase in the number of batteries.

As illustrated in FIG. 6, the LED irradiation timing continuously drives the LED 71 by passing a maximum current to the LED 71 only during a first predetermined time from time T0 when a measurement of the body temperature of an object completes to time T1 when 10 seconds elapse after time T0, so that the liquid crystal display part 5 is irradiated with backlight of maximum light quantity to make the displayed body temperature bright and easily visible. The body temperature brightly displayed is easy to read even in the dark.

During a second predetermined time such as 30 seconds from time T1 to time T2, the LED 71 is intermittently driven at a predetermined ON/OFF ratio, for example, an ON/OFF ratio of about $\frac{1}{3}$ as illustrated in FIG. 6, to reduce the light quantity to about $\frac{1}{3}$ of the maximum light quantity and dim the LED 71 so that the displayed body temperature is somehow visible, thereby reducing power consumption. After time T2, the LED 71 is stopped so that no backlight is emitted from the LED 71.

To make the LED 71 of the backlight emitting part 7 achieve the above-mentioned operation, the MCU 1 sets the output inhibit signals SK1 and SK2 of the input/output ports P1 and P2 to "0". Thereafter, from time T0 to T1 in FIG. 6, the MCU 1 continuously passes a current to the LED 71 to maximize the backlight quantity of the LED 71 by supplying "0" as the output signals SD1 and SD2 of the input/output ports P1 and P2 to the first inputs of the NOR circuits 113 and 123. As a result, the outputs from the NOR circuits 113 and 123 become "1" to turn on the MOSFETs 111 and 121 of the input/output ports P1 and P2.

When the MOSFETs 111 and 121 of the input/output ports P1 and P2 are turned on, the LED 71 of the backlight emitting part 7 receives a current from the voltage VDD through a route extending along the resistor 75, LED 71, MOSFETs 111 and 121, and the ground. As a result, the LED 71 emits light, which irradiates as backlight the liquid crystal display part 5 so that, during the time of, for example, 10 seconds from T0 to T1, the body temperature displayed on the liquid crystal display part 5 becomes visible even in the dark. The current passed to the LED 71 through the above-mentioned route has a value obtained by subtracting an ON voltage VD71 of the LED 71 from the voltage VDD and dividing the difference by a resistance value of the resistor 75, if voltage drops at the input/output ports P1 and P2 are ignored.

To drive the LED 71 and emit light therefrom, only the MOSFET 111 at the input/output port P1 may be turned on. Turning on the two MOSFETs 111 and 121 at the two input/output ports P1 and P2 can reduce the influence of internal resistance, i.e., voltage drops at the MOSFETs 111 and 121. In the above-mentioned operation, the input enable signals SP1 and SP2 of the input/output ports P1 and P2 are not directly related to the operation, and therefore, may take any values.

In a period from time T1 to T2 after T1 in FIG. 6, the MCU 1 reduces the amount of the backlight from the LED 71 to the liquid crystal display part 5 to about $\frac{1}{3}$ of the maximum light quantity, thereby reducing power consumption. For this, the LED 71 is intermittently driven at ON/OFF ratio of about $\frac{1}{3}$.

To carry out the intermittent operation at the ON/OFF ratio of about $\frac{1}{3}$, the MCU 1 provides, from the input/output ports P1 and P2, the first inputs of the NOR circuits 113 and 123 with the output signals SD1 and SD2 that intermittently repeat ON and OFF at the ON/OFF ratio of about $\frac{1}{3}$. The output signals SD1 and SD2 having the ON/OFF ratio of about $\frac{1}{3}$ control ON/OFF of the MOSFETs 111 and 121, thereby driving the LED 71 according to the ON/OFF operation of the MOSFETs 111 and 121. As a result, the quantity of the backlight from the LED 71 decreases to about $\frac{1}{3}$ of the light quantity at the maximum current. The body temperature displayed on the liquid crystal display part 5 irradiated with the backlight whose quantity is reduced to about $\frac{1}{3}$ is dim so that it is somehow visible. This results in reducing power consumption.

A repetition frequency of the output signals SD1 and SD2 that are intermittently turned on and off at the ON/OFF ratio of about $\frac{1}{3}$ is preferably 30 Hz or higher so that the ON and OFF of the LED 71 driven by the output signals SD1 and SD2 are not sensed by human eyes.

After time T2, for example, 30 seconds after time T0 when the body temperature is started to be displayed with the liquid crystal, the MCU 1 stops driving the LED 71 of the backlight emitting part 7, to stop the backlight irradiation of the liquid crystal display part 5 by the LED 71, thereby completely stopping power consumption by the backlight emitting part 7.

A power ON soft start operation according to the embodiment will be explained with reference to FIG. 7. The power ON soft start operation of the embodiment is achieved when the start switch 9 illustrated in FIG. 1 is operated to issue an interrupt to the MCU 1, so that the MCU 1, more precisely, a program stored in a memory of the MCU 1 supplies the operation voltage VCC from the voltage VDD to the body temperature measuring part 3. This power ON soft start operation is carried out by switching internal circuits related to the input/output ports P3, P4, and P5 of the MCU 1. According to the embodiment, the three input/output ports P3, P4, and P5 are connected in parallel, to reduce a voltage drop at a p-channel MOSFET 137 (to be explained later) that is a switching element to supply the operation voltage VCC from the voltage VDD to the body temperature measuring part 3.

The internal circuits related to the input/output ports P3, P4, and P5 of the MCU 1 have the same configuration. Accordingly, FIG. 7 illustrates only the input/output port P3. Each having this configuration, the three input/output ports P3, P4, and P5 are connected in parallel to the capacitor 15. A voltage across the capacitor 15 is supplied as the operation voltage VCC to the body temperature measuring part 3. As mentioned above, the capacitor 15 is a decoupling capacitor for the body temperature measuring part 3, to reduce the impedance of the power source that supplies the operation voltage VCC to the body temperature measuring part 3.

Figure 7:
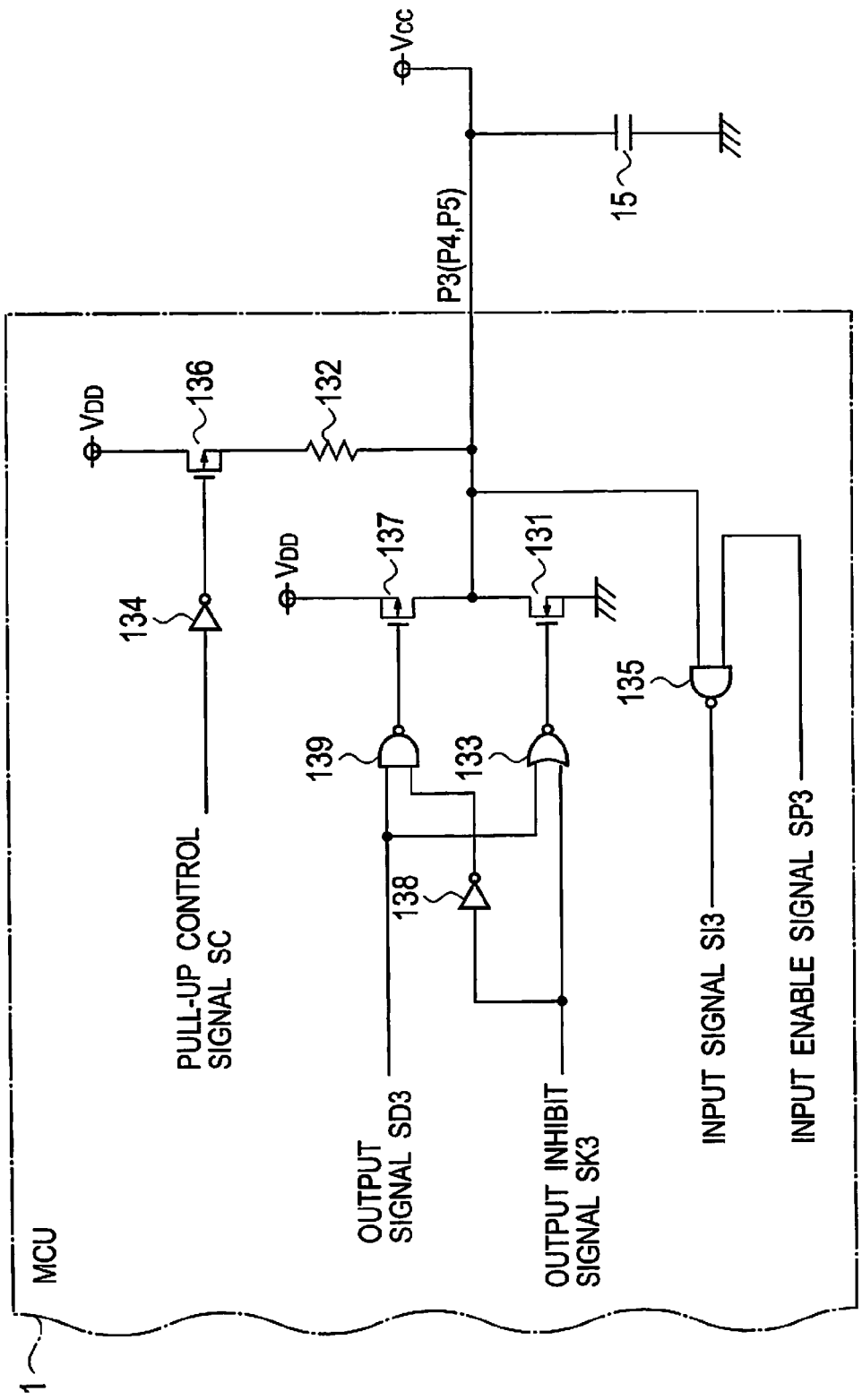
FIG. 7 is a circuit diagram illustrating the inside of the input/output port of the MCU relating to a power ON soft start in the ear thermometer of the embodiment illustrated in FIG. 1.

In the internal circuit of the input/output port P3 illustrated in FIG. 7, the input/output port P3 is connected to a connection point between a drain of an n-channel MOSFET 131 and a drain of the p-channel MOSFET 137. A source of the MOSFET 131 is grounded and a source of the MOSFET 137 is connected to the voltage VDD. When the MOSFET 137 turns on, the voltage VDD connected to the drain of the MOSFET 137 is supplied as the operation voltage VCC through the MOSFET 137 and the input/output port P3 to the body temperature measuring part 3.

A gate of the MOSFET 131 is connected to an output of a NOR circuit 133. A first input of the NOR circuit 133 receives an output signal SD3 and a second input thereof receives an output inhibit signal SK3. A gate of the MOSFET 137 is connected to an output of a NAND circuit 139. A first input of the NAND circuit 139 receives the output signal SD3 and a second input thereof receives the output inhibit signal SK3 through an inverter 138.

The input/output port P3 is pulled up to the voltage VDD through a series circuit including a resistor 132 and a p-channel MOSFET 136. A gate of the MOSFET 136 receives through an inverter 134 a pull-up control signal SC. The input/output port P3 is also connected to a first input of a NAND circuit 135. A second input of the NAND circuit 135 receives an input enable signal SP3 and the NAND circuit 135 outputs an input signal 513 as an output signal.

With the above-mentioned circuit configuration, the power ON soft start operation is started when an object operates the start switch 9 illustrated in FIG. 1 so that the start switch 9 issues an interrupt to the MCU 1 and the MCU 1 starts the operation.

First, the MCU 1 sets the output inhibit signal SK3 illustrated in FIG. 7 to "0" and the output signal SD3 of the input/output port P3 to "1". As a result, the output inhibit signal SK3 of "0" supplies "0" to the second input of the NOR circuit 133 and "1" to the second input of the NAND circuit 139 through the inverter 138. This releases a write inhibited state of the input/output port P3. According to the output signal SD3 of "1", the NAND circuit 139 outputs "0" to turn on the MOSFET 137 and the NOR circuit 133 outputs "0" to turn off the MOSFET 131.

When the MOSFET 137 becomes ON and the MOSFET 131 OFF, the voltage VDD supplied to the drain of the MOSFET 137 charges the capacitor 15 through the MOSFET 137 and input/output port P3. The voltage VDD and the voltage of the capacitor 15 are supplied as the voltage VCC to the body temperature measuring part 3. This state is referred to as a voltage supplying state of MOSFET 137=ON and MOSFET 131=OFF.

In the voltage supplying state of MOSFET 137=ON and MOSFET 131=OFF, the output inhibit signal SK3 is set to "1". Then, the NAND circuit 139 outputs "1" and the NOR circuit 133 outputs "0", to turn off the MOSFETs 137 and 131. The voltage VDD supplied to the drain of the MOSFET 137 is blocked by the MOSFET 137 that is OFF, so that the capacitor 15 is not charged and the voltage VCC is not supplied to the body temperature measuring part 3. This state is referred to as a voltage not-supplying state of MOSFET 137=OFF and MOSFET 131=OFF.

Figure 8:
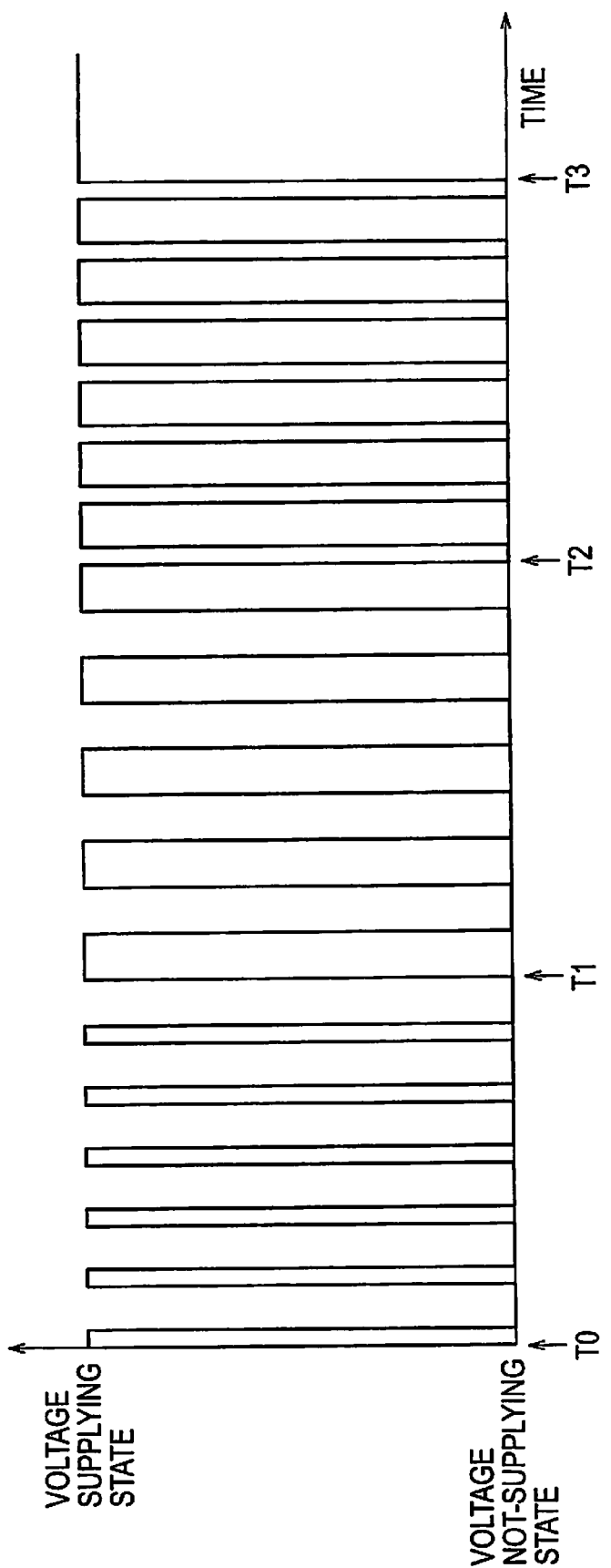
FIG. 8 is a timing chart illustrating the power ON soft start operation.

FIG. 8 illustrates timing of gradually increasing a ratio of the voltage supplying state of MOSFET 137=ON and MOSFET 131=OFF to the voltage not-supplying state of MOSFET 137=OFF and MOSFET 131=OFF, and thereafter, continuing a voltage supplying state, thereby conducting the power ON soft start operation.

In FIG. 8, the voltage supplying state and voltage not-supplying state intermittently repeat like pulses. More precisely, operating the start switch 9 issues an interrupt to the MCU 1, so that the MCU 1 starts the power ON soft start operation at time T0. For a first predetermined time from T0 to T1, the ratio of the voltage supplying state to the voltage not-supplying state is low, for example, about ¼ to reduce the supply of the voltage VDD. Shortening the time for the voltage supplying state results in relaxing a rush current to charge the capacitor 15 from the voltage VDD through the MOSFET 137. The capacitor 15, therefore, is gradually charged toward the voltage VCC, thereby start the power ON soft start operation.

In the next predetermined time from T1 to T2, the ratio of the voltage supplying state to the voltage not-supplying state is increased to, for example, about ½, to increase the supply of the voltage VDD. In the next predetermined time from T2 to T3, the ratio of the voltage supplying state to the voltage not-supplying state is further increased to, for example, about ¾, to further increase the supply of the voltage VDD. In this way, the charging of the capacitor 15 is gradually increased toward the voltage VCC. After time T3, the voltage supplying state is increased to 100% to continuously supply the voltage VDD.

In this way, the ratio of the voltage supplying state to the voltage not-supplying state is gradually increased like ¼, ½, and ¾, and lastly, the voltage is continuously supplied. This power ON soft start operation greatly reduces a voltage drop in the voltage VDD of the battery at the start of power ON.

Figure 10:
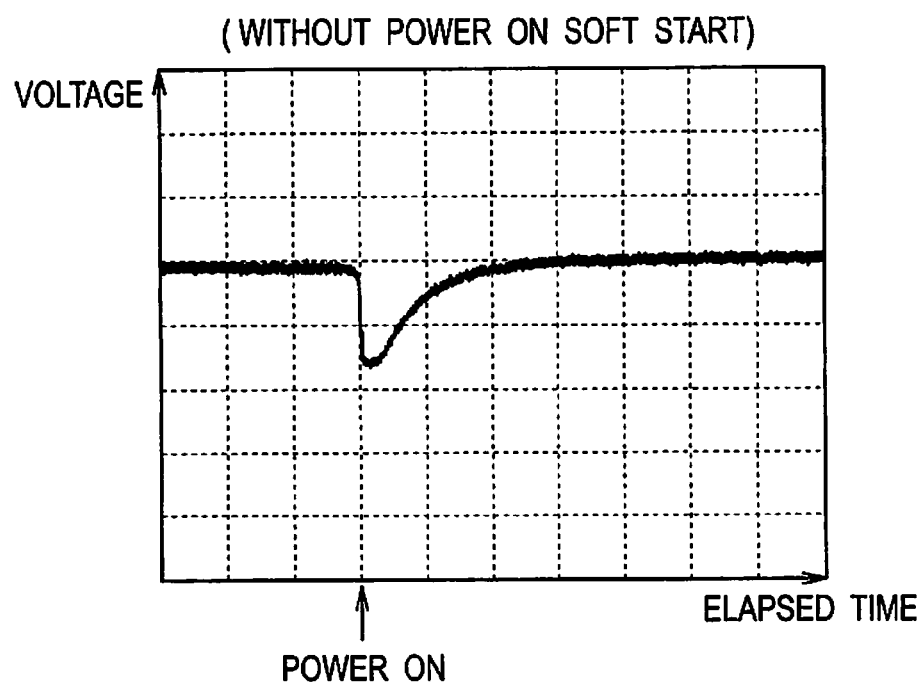
FIG. 10 is a voltage waveform diagram illustrating a voltage drop in the voltage VDD when the power ON soft start operation is not carried out.

In more detail, FIG. 10 is a voltage waveform diagram illustrating a voltage drop in the voltage VDD supplied as the voltage VCC to the body temperature measuring part 3 at the power ON start without the power ON soft start operation. In FIG. 10, a momentary voltage drop is observed for about 1 ms in the voltage VDD.

This voltage drop occurs when the MOSFET 137 turns on to charge the capacitor 15. This voltage drop indicates that the battery 11 for charging the capacitor 15 discharges to increase the internal impedance of the battery 11 and the capacitor 13 connected in parallel with the battery 11 is unable to prevent the increase in the internal impedance of the battery 11. If this happens, an internal voltage detection circuit of the MCU 1 operates to establish a reset state that prevents the power ON start operation, destabilizes the operation of the ear thermometer, and prevents the ear thermometer from conducting the necessary number of measurements. It is important, therefore, to surely carry out the power ON soft start operation. A time necessary for conducting the power ON soft start operation, i.e., a time for charging the capacitor 15 is about 0.2 seconds. Such a time required by the power ON soft start operation causes no trouble.

Figure 9:
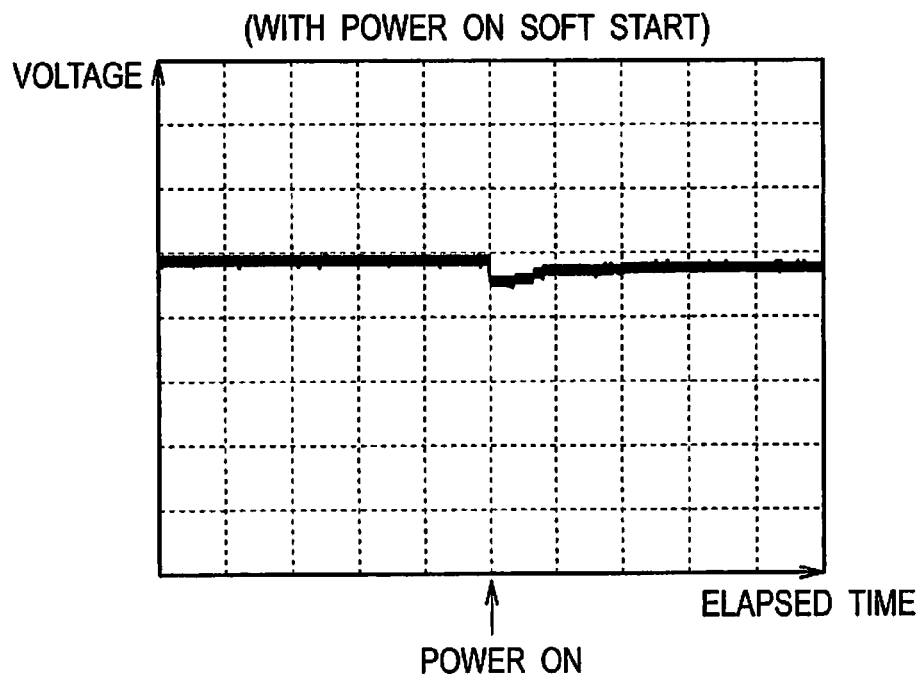
FIG. 9 is a voltage waveform diagram illustrating a voltage drop in a voltage VDD when the power ON soft start operation is carried out.

FIG. 9 is a voltage waveform diagram illustrating a voltage drop in the voltage VDD when the above-mentioned power ON soft start operation is carried out. As is apparent in FIG. 9, the power ON soft start operation greatly reduces a voltage drop in the voltage VDD of the battery 11.

Figure 11:
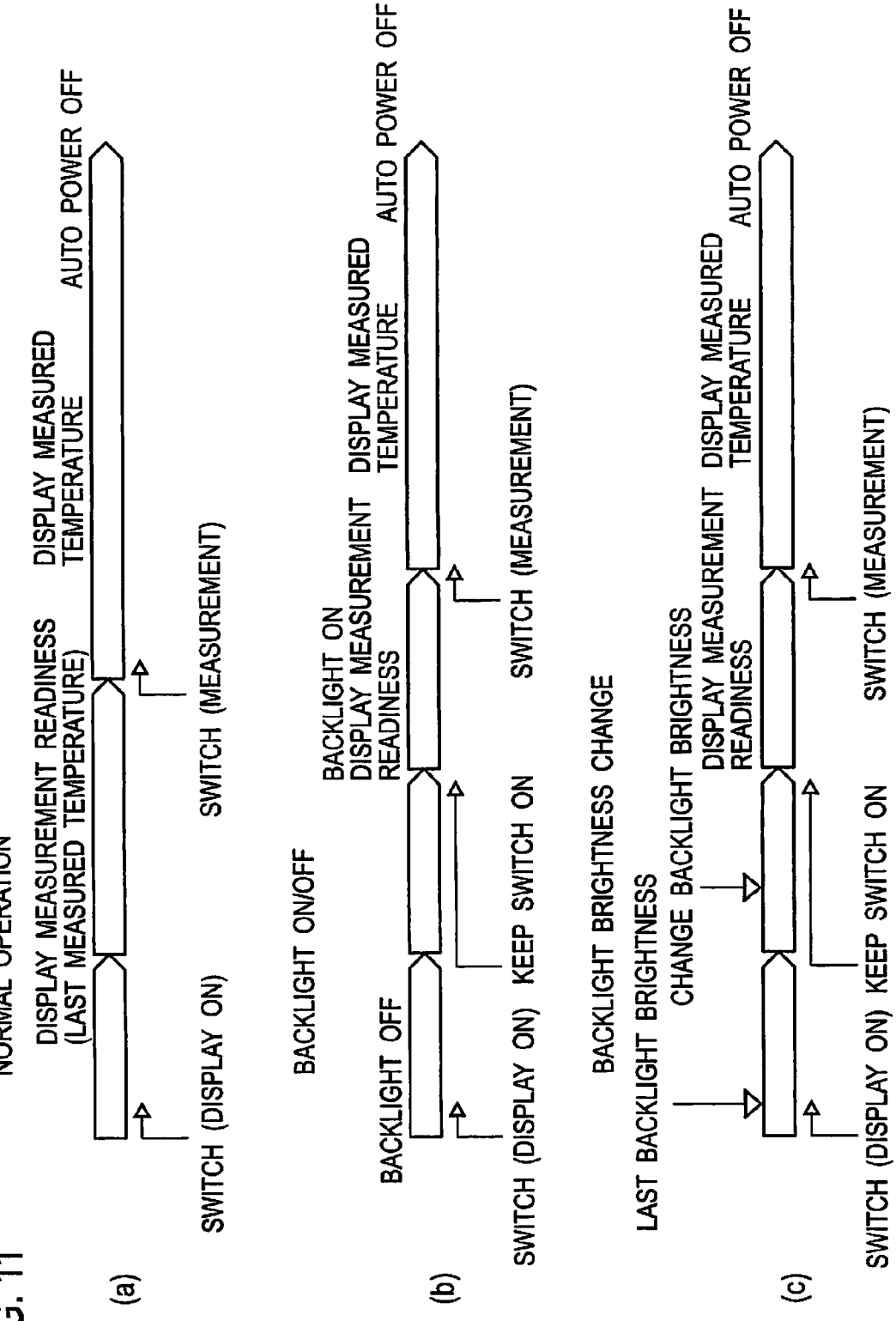
FIG. 11 is a timing chart illustrating switch operations and related operating states.

As mentioned above, the MCU 1 receives an interrupt when the start switch 9 is operated, and then, starts various operations including the power ON soft start operation and body temperature measuring operation. In this way, the single start switch 9 serves as a switch for the power ON soft start operation and a switch for the body temperature measuring operation. As illustrated in FIG. 11, the MCU 1 is activated by the interrupt from the start switch 9. Thereafter, the MCU 1 monitors operation of the start switch 9 and determines whether the start switch 9 has been pushed for a long time, or has momentarily been pushed, or has continuously been pushed longer than a predetermined time. According to the determination that the start switch 9 has been pushed for a long time, or has momentarily been pushed, or has continuously been pushed longer than the predetermined time, the MCU 1 selectively carries out an operation of changing the maximum light quantity, an operation of using the backlight, and the like.

FIG. 11(a) illustrates a normal operation. When the start switch 9 is momentarily pushed, the liquid crystal turns on, the backlight turns on, and a temperature measurement readiness or a last measurement value is displayed. If the momentary switch ON operation is repeated, a temperature measurement starts, a measured temperature is brightly displayed, the backlight dims as time elapses, and the backlight turns off.

In FIG. 11(b), the start switch 9 is momentarily pushed and the backlight turns off. When the start switch 9 is pushed for a long time, the backlight turns on and the temperature measurement readiness is brightly displayed. If the start switch 9 is again momentarily pushed, a temperature measurement starts, a measured temperature is brightly displayed, the backlight dims as time passes, and the backlight turns off. If the start switch 9 is again pushed for a long time with the backlight being bright, the backlight turns off. Namely, this example turns on and off the backlight according to the long push of the start switch 9.

In FIG. 11(c), the start switch 9 is momentarily pushed, and thereafter, is continuously pushed. Depending on the pushed time, the brightness of the backlight increases up to the maximum level and then decreases. If the start switch 9 is momentarily pushed thereafter, a temperature measurement starts, a measured temperature is brightly displayed, the backlight dims as time passes, and the backlight turns off.

With reference to FIGS. 12 to 15, a drive circuit of a liquid crystal display used for portable compact equipment such as a handy measurement device, a handy medical device, and a handy health device will be explained.

To drive a liquid crystal display with a microcontroller, there are a method of arranging a liquid crystal display controller as external hardware of the microcontroller and a method of using a microcontroller incorporating a liquid crystal display controller. Generally, to reduce the number of parts, size, and price of an electronic device, a one-chip microcontroller is used. Accordingly, an electronic device provided with a liquid crystal display usually employs the microcontroller incorporating a liquid crystal display controller. Most of microcontrollers in the market, however, are without liquid crystal display controllers. The microcontrollers incorporating liquid crystal display controllers are limited in their types and are hardly selectable, to restrict the degree of freedom in designing circuits. On the other hand, the method of arranging a liquid crystal display controller as external hardware increases the number of parts, a package area, and a manufacturing cost.

The drive circuit for a liquid crystal display according to the embodiment solves these technical problems and is capable of directly driving the liquid crystal display even with the microcontroller not incorporating a liquid crystal display controller, with a minimum number of parts without enlarging a package area.

Comparing the microcontroller incorporating a liquid crystal display controller with the microcontroller not incorporating a liquid crystal display controller of the same ability, the microcontroller incorporating a liquid crystal display controller is higher in cost because the liquid crystal display controller increases a chip area. On the other hand, the drive circuit for a liquid crystal display according to the embodiment is advantageous on the cost front.

Figure 12:
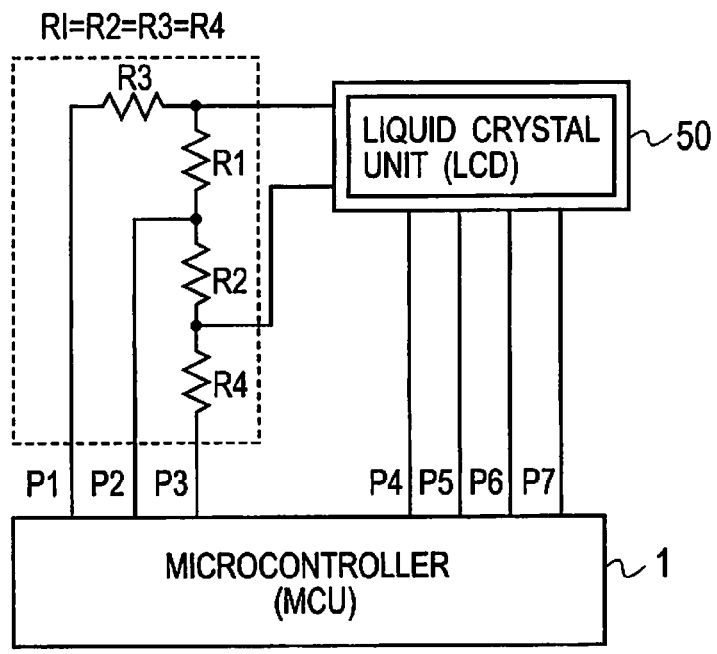
FIG. 12 is a view illustrating an embodiment of a drive circuit of a ½-duty liquid crystal display.

As illustrated in FIG. 12, the drive circuit for a ½-duty liquid crystal display has a microcontroller (MCU) 1, a liquid crystal unit (LCD) 50, and a set of voltage dividing resistors R1 to R4 interposed between the microcontroller 1 and the liquid crystal unit 50. Output ports P1, P2, and P3 of the microcontroller 1 are controlled by an internal program of the microcontroller, to output rectangular waves having a phase difference of $\pi/4$ (90°). The voltage dividing resistors R1 to R4 have the same resistance value and are connected in series in the order of R3, R1, R2, and R4. The output port P1 of the microcontroller 1 is connected to an open end of the voltage dividing register R3, the output port P2 between the voltage dividing resistors R1 and R2, and the output port P3 to an open end of the voltage dividing resistor R4.

Figure 13:
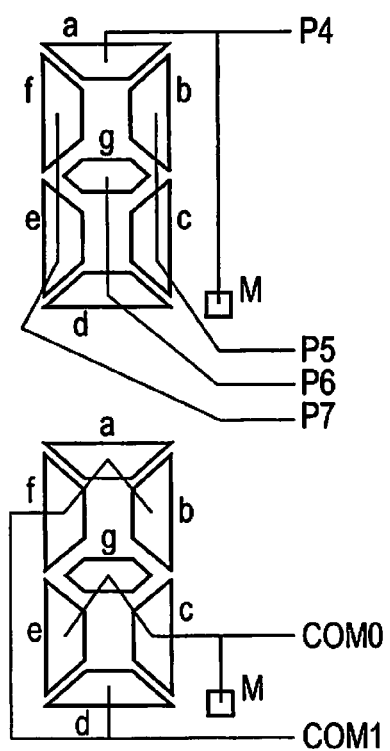
FIG. 13 is a view illustrating a wiring example of a 7-segment liquid crystal display.

As illustrated in FIG. 13, the liquid crystal unit 50 has seven liquid crystal segments A to G to display, generally, numbers and a liquid crystal segment M to display, generally, a decimal point. A common port COM0 of the liquid crystal unit 50 is connected to the liquid crystal segments C, E, G, and M and a common port COM1 to the liquid crystal segments A, B, D, and F. The common ports COM0 and COM1 are also connected between the voltage dividing resistors R3 and R1 and between the voltage dividing resistors R2 and R4. An output port P4 of the microcontroller 1 is connected to the liquid crystal segments A and M, an output port P5 to the liquid crystal segments B and C, an output port P6 to the liquid crystal segments D and G, and an output port P7 to the liquid crystal segments E and F.

The output ports P1, P2, and P3 of the microcontroller 1 are controlled by the internal program of the microcontroller, to output rectangular waves delayed by $\pi/4$ (90°), respectively. The outputs from the output ports P1, P2, and P3 are divided by the voltage dividing resistors R1, R3, R3, and R4, to provide the common ports COM0 and COM1 of the liquid crystal unit 2 with signals. The output ports P4, P5, P6, and P7 are controlled by the internal program of the microcontroller 1, to output drive signals corresponding to the common ports COM0 and COM1 in synchronization with operation timing, thereby turning on/off optional liquid crystal segments. This will be explained in detail with reference to FIG. 14.

Figure 14:
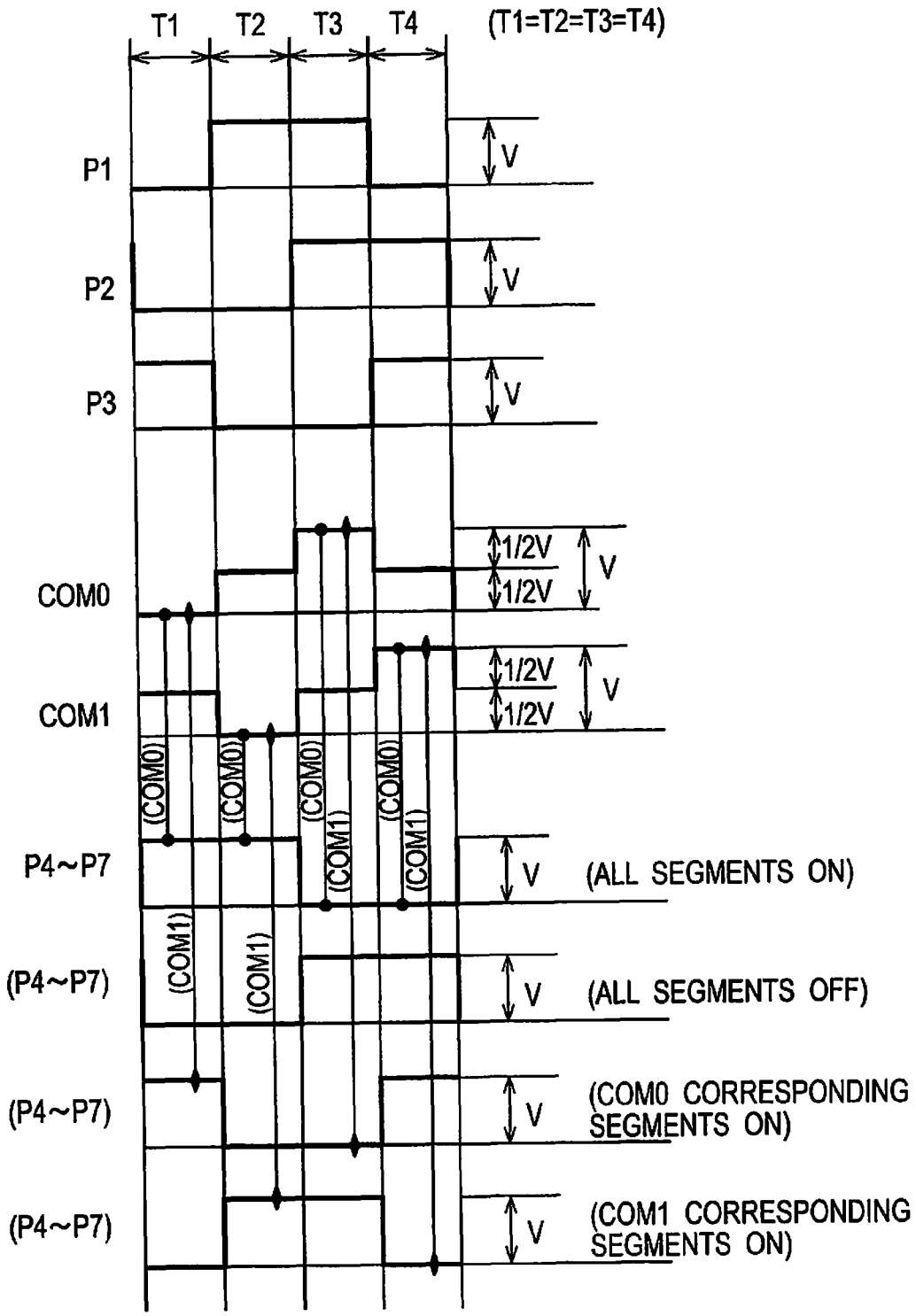
FIG. 14 is a view illustrating operation timing of the wiring example of FIG. 13.

FIG. 14 illustrates operation timing. Timings T1, T2, T3, and T4 have the same interval, and therefore, "T1+T2+T3+T4" from T1 to T4 is equal to "T1×4". The output ports P1 to P3 each output a predetermined voltage value V or 0 (these voltage values being expressed as "1" and "0" hereunder) as mentioned below.

A) At timing T1, "0" from P1, "0" from P2, and "1" from P3
B) At timing T2, "1" from P1, "0" from P2, and "0" from P3
C) At timing T3, "1" from P1, "1" from P2, and "0" from P3
D) At timing T4, "0" from P1, "1" from P2, and "1" from P3

As a result, the below-mentioned voltage values appear at the common ports COM0 and COM1.

A) At timing T1, "0" at COM0 and ½ V at COM1
B) At timing T2, ½ V at COM0 and "0" at COM1
C) At timing T3, "1" at COM0 and ½ V at COM1
D) At timing T4, ½ V at COM0 and "1" at COM1

At this time, the liquid segments A to G and M connected to the common ports COM0 and COM1 will entirely be turned on if the output ports P4 to P7 output the below-mentioned values.

A) At timing T1, "1"
B) At timing T2, "1"
C) At timing T3, "0"
D) At timing T4, "0"

On the other hand, all of the liquid crystal segments A to G and M connected to the common ports COM0 and COM1 will be turned off if the output ports P4 to P7 output the below-mentioned values that are opposite to those mentioned above.

A) At timing T1, "0"
B) At timing T2, "0"
C) At timing T3, "1"
D) At timing T4, "1"

To turn on only the liquid crystal segments C, E, G, and M connected to the common port COM0, the output ports P4 to P7 output the below-mentioned values.

A) At timing T1, "1"
B) At timing T2, "0"
C) At timing T3, "0"
D) At timing T4, "1"

To turn on only the liquid crystal segments A, B, D, and F connected to the common port COM1, the output ports P4 to P7 output the below-mentioned values.

A) At timing T1, "0"
B) At timing T2, "1"
C) At timing T3, "1"
D) At timing T4, "0"

Figure 15:
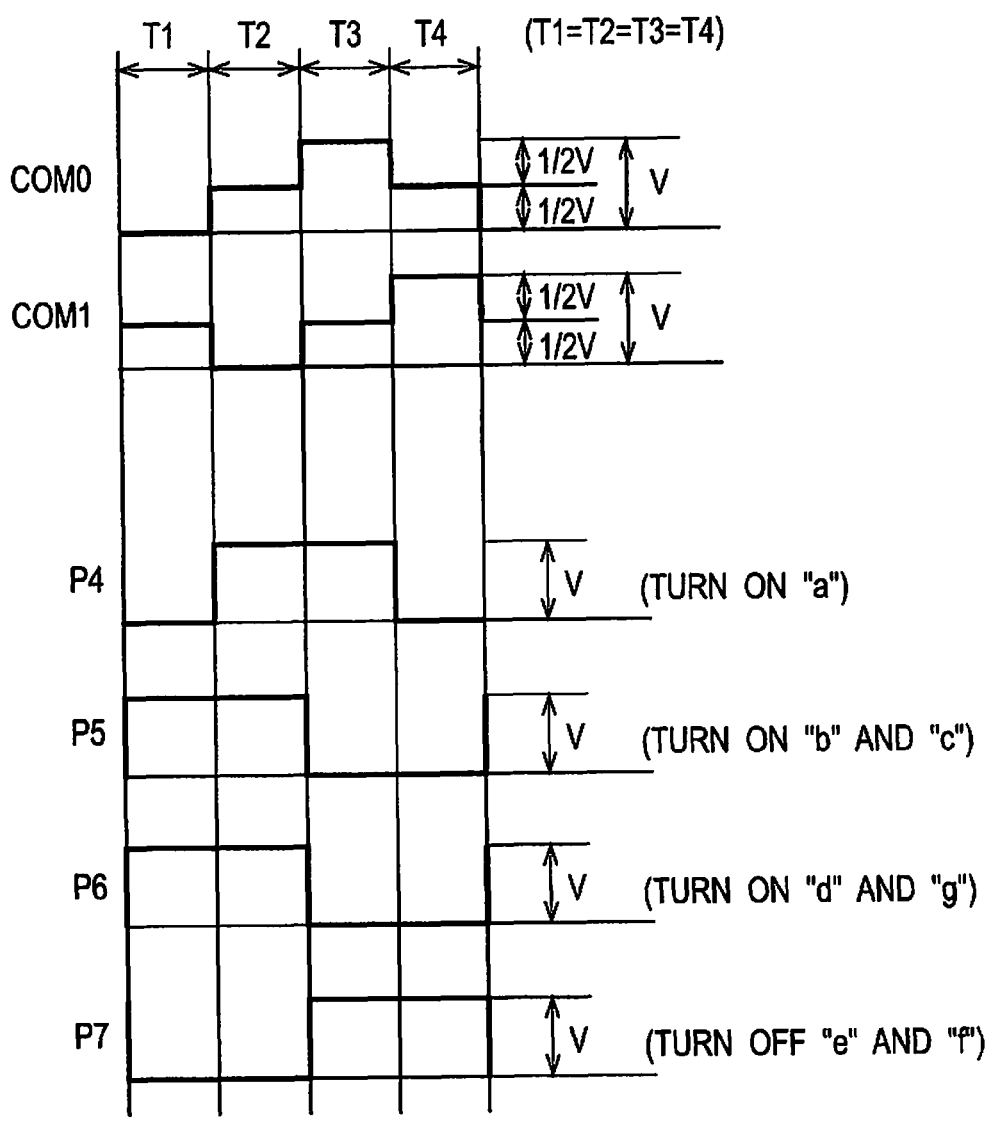
FIG. 15 is a view illustrating timing to display a number "3" with the wiring example of FIG. 13.

FIG. 15 illustrates timing and port outputs to display a number "3" on the liquid crystal display of FIG. 13.

Among the liquid crystal segments A to D and G necessary for displaying the number "3", the liquid crystal segments G and C are driven at the timing of driving the common port COM0 and the liquid crystal segments A, B, and D at the timing of driving the common port COM1. At timings T1 to T4, the ports P4 to P7 output the below-mentioned voltage values to drive the liquid crystal segments A to D and G.

1) The output port P4 outputs "0" at timing T1, "1" at T2, "1" at T3, and "0" at T4, to turn on the liquid crystal segment A.
2) The output port P5 outputs "1" at timing T1, "1" at T2, "0" at T3, and "0" at T4, to turn on the liquid crystal segments B and C.
3) The output port P6 outputs "1" at timing T1, "1" at T2, "0" at T3, and "0" at T4, to turn on the liquid crystal segments D and G.
4) The output port P7 outputs "0" at timing T1, "0" at T2, "1" at T3, and "1" at T4, to turn off the liquid crystal segments E and F.

The other numbers and numbers with decimal points are similarly displayed by combining values outputted from the ports P4 to P7 at the timings T1 to T4 and turning on/off the liquid crystal segments.

INDUSTRIAL APPLICABILITY

The present invention provides an ear thermometer capable of displaying a body temperature with liquid crystal irradiated with backlight so that the body temperature is easily visible even in a dark place without increasing a battery capacity. This ear thermometer is only inserted into an ear hole, to easily and quickly measure a body temperature and is applicable to an industrial field of body temperature measuring devices.

DESCRIPTION OF REFERENCE NUMERALS

1: MCU
3: Body temperature measuring part
5: Liquid crystal display part
7: Backlight emitting part
9: Start switch
11: Battery
13, 15: Capacitor
31: Thermopile infrared sensor
31A: Thermopile
31B: Thermistor
33: A-D conversion circuit
71: Light emitting diode (LED)
73: Light guide
75, 77: Resistor
111, 123, 131, 136, 137: MOSFET
113, 123, 133: NOR circuit
115, 125, 135, 139: NAND circuit
134, 138: Inverter
P1-P6: Input/output port of MCU

The invention claimed is:

1. An ear thermometer comprising:
a body temperature measuring part to sense infrared rays radiated from an ear hole depth and thereby measure a body temperature;
a liquid crystal display part to display the body temperature measured by the body temperature measuring part;
a backlight emitting part to irradiate the liquid crystal display part with backlight;
a driving-controlling part to display the body temperature measured by the body temperature measuring part on the liquid crystal display part and drive the backlight emitting part so that the quantity of the backlight that irradiates the liquid crystal display part from the backlight emitting part may gradually change from a maximum level to an off level; and
a power supply control part that intermittently carries out power supply to the body temperature measuring part for a predetermined time from the start of power supply to the body temperature measuring part by gradually increasing a predetermined small ON/OFF ratio to a predetermined large ON/OFF ratio, and after the predetermined time elapses, continuously carries out power supply to the body temperature measuring part.

2. The ear thermometer as set forth in claim 1, wherein:
the backlight emitting part has a light emitting diode.

3. An ear thermometer comprising:
a body temperature measuring part to sense infrared rays radiated from an ear hole depth and thereby measure a body temperature;

a liquid crystal display part to display the body temperature measured by the body temperature measuring part;

a backlight emitting part to irradiate the liquid crystal display part with backlight;

a driving-controlling part to display the body temperature measured by the body temperature measuring part on the liquid crystal display part and drive the backlight emitting part so that the quantity of the backlight that irradiates the liquid crystal display part from the backlight emitting part may gradually change from a maximum level to an off level; and a power supply control part that supplies power to the body temperature measuring part intermittently at a first predetermined ON/OFF ratio for a first predetermined time from the start of power supply, intermittently at a second predetermined ON/OFF ratio that is larger than the first predetermined ON/OFF ratio for a second predetermined time that follows the first predetermined time, intermittently at a third predetermined ON/OFF ratio that is larger than the second predetermined ON/OFF ratio for a third predetermined time that follows the second predetermined time, and continuously after the third predetermined time elapses.

4. The ear thermometer as set forth in claim 3, wherein:
the backlight emitting part has a light emitting diode.

5. The ear thermometer as set forth in claim 3, wherein:
the intermittent drive control on the backlight emitting part by the driving-controlling part at the predetermined ON/OFF ratio is carried out at a repetition frequency of 30 Hz or greater.

6. An ear thermometer comprising:
a body temperature measuring part to sense infrared rays radiated from an ear hole depth and thereby measure a body temperature;

a liquid crystal display part to display the body temperature measured by the body temperature measuring part;

a backlight emitting part to irradiate the liquid crystal display part with backlight;

a driving-controlling part to display the body temperature measured by the body temperature measuring part on the liquid crystal display part, drive and control the backlight emitting part so that, for a first predetermined time from the start of the display, the light quantity of the backlight irradiating the liquid crystal display part from the backlight emitting part is at a maximum level, drive and control the backlight emitting part so that, for a second predetermined time following the first predetermined time, the light quantity of the backlight irradiating the liquid crystal display part from the backlight emitting part is at a predetermined level lower than the maximum level, and drive and control the backlight emitting part so that, once the second predetermined time elapses, the light quantity of the backlight irradiating the liquid crystal display part from the backlight emitting part is zeroed; and a power supply control part that intermittently carries out power supply to the body temperature measuring part for a predetermined time from the start of power supply to the body temperature measuring part by gradually increasing a predetermined small ON/OFF ratio to a predetermined large ON/OFF ratio, and after the predetermined time elapses, continuously carries out power supply to the body temperature measuring part.

7. The ear thermometer as set forth in claim 6, wherein:
the driving-controlling part controls the backlight emitting part so that, for the first predetermined time, the liquid crystal display part is continuously irradiated with the backlight, intermittently controls the backlight emitting part at a predetermined ON/OFF ratio so that, for the second predetermined time, the liquid crystal display part is intermittently irradiated with the backlight at the predetermined ON/OFF ratio, and controls the backlight emitting part so that, once the second predetermined time elapses, the backlight irradiating the liquid crystal display part is turned off.

8. The ear thermometer as set forth in claim 6, wherein:
the backlight emitting part has a light emitting diode.

9. The ear thermometer as set forth in claim 8, wherein:
the driving-controlling part controls the backlight emitting part at a predetermined ON/OFF ratio so that, for the second predetermined time, the liquid crystal display part is irradiated with the backlight at a repetition frequency of 30 Hz or over.

10. An ear thermometer comprising:
a body temperature measuring part to sense infrared rays radiated from an ear hole depth and thereby measure a body temperature;

a liquid crystal display part to display the body temperature measured by the body temperature measuring part;

a backlight emitting part to irradiate the liquid crystal display part with backlight;

a driving-controlling part to display the body temperature measured by the body temperature measuring part on the liquid crystal display part, drive and control the backlight emitting part so that, for a first predetermined time from the start of the display, the light quantity of the backlight irradiating the liquid crystal display part from the backlight emitting part is at a maximum level, drive and control the backlight emitting part so that, for a second predetermined time following the first predetermined time, the light quantity of the backlight irradiating the liquid crystal display part from the backlight emitting part is at a predetermined level lower than the maximum level, and drive and control the backlight emitting part so that, once the second predetermined time elapses, the light quantity of the backlight irradiating the liquid crystal display part from the backlight emitting part is zeroed; and a power supply control part that supplies power to the body temperature measuring part intermittently at a first predetermined ON/OFF ratio for a first predetermined time from the start of power supply, intermittently at a second predetermined ON/OFF ratio that is larger than the first predetermined ON/OFF ratio for a second predetermined time that follows the first predetermined time, intermittently at a third predetermined ON/OFF ratio that is larger than the second predetermined ON/OFF ratio for a third predetermined time that follows the second predetermined time, and continuously after the third predetermined time elapses.

11. The ear thermometer as set forth in claim 10, wherein:
the backlight emitting part has a light emitting diode.

12. The ear thermometer as set forth in claim 10, wherein:
the intermittent drive control on the backlight emitting part by the driving-controlling part at the predetermined ON/OFF ratio is carried out at a repetition frequency of 30 Hz or greater.

* * * * *